(12) United States Patent
Smirthwaite

(10) Patent No.: US 10,188,523 B2
(45) Date of Patent: *Jan. 29, 2019

(54) PROSTHETIC ANKLE COMPONENTS

(71) Applicant: Biomet UK Healthcare Limited, Bridgend (GB)

(72) Inventor: Paul Smirthwaite, Bath (GB)

(73) Assignee: Biomet UK Healthcare Limited, Bridgend (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/485,647

(22) Filed: Apr. 12, 2017

(65) Prior Publication Data
US 2017/0216041 A1    Aug. 3, 2017

Related U.S. Application Data

(63) Continuation of application No. 14/390,202, filed as application No. PCT/GB2013/050885 on Apr. 4, 2013, now Pat. No. 9,655,734.

(30) Foreign Application Priority Data

Apr. 5, 2012  (GB) .................................. 1206127.1

(51) Int. Cl.
*A61F 2/42* (2006.01)
*A61F 2/30* (2006.01)

(52) U.S. Cl.
CPC ...... *A61F 2/4202* (2013.01); *A61F 2002/304* (2013.01); *A61F 2002/3038* (2013.01);
(Continued)

(58) Field of Classification Search
CPC ............ A61F 2/4202; A61F 2002/4205; A61F 2002/4207; A61F 2002/30172;
(Continued)

(56) References Cited

U.S. PATENT DOCUMENTS 6,228,124 B1    5/2001   Slemker et al.
7,462,201 B2   12/2008   Christensen
(Continued)

FOREIGN PATENT DOCUMENTS

CN    101534751 A    9/2009
EP      1506752 A1    2/2005
(Continued)

OTHER PUBLICATIONS

"Australian Application Serial No. 2013245411, First Examiners Report dated Oct. 13, 2016", 3 pgs.
(Continued)

*Primary Examiner* — Brian Dukert
(74) *Attorney, Agent, or Firm* — Schwegman Lundberg & Woessner, P.A.

(57) ABSTRACT

A first prosthetic ankle component (10) comprising: a first bearing surface (12) configured to engage a second bearing surface (22) of a second prosthetic ankle component (20); and a protrusion (16) or slot (26) on the first bearing surface, the protrusion or slot being configured to engage a respective slot (26) or protrusion (16) in the second bearing surface of the second prosthetic ankle component, wherein the protrusion or slot is further configured such that the interaction with the respective slot or protrusion permits the first and second prosthetic ankle components to slide with respect to one another in an interface plane defined by the interface between the first and second bearing surfaces, and wherein the protrusion or slot is further configured to restrict the first and second prosthetic ankle components moving away from one another in a direction with a component perpendicular to the interface plane.

14 Claims, 8 Drawing Sheets

(52) U.S. Cl.
CPC .......... *A61F 2002/3039* (2013.01); *A61F 2002/30168* (2013.01); *A61F 2002/30172* (2013.01); *A61F 2002/30299* (2013.01); *A61F 2002/30364* (2013.01); *A61F 2002/30387* (2013.01); *A61F 2002/30398* (2013.01); *A61F 2002/30604* (2013.01); *A61F 2002/30878* (2013.01); *A61F 2002/30884* (2013.01); *A61F 2002/4205* (2013.01); *A61F 2002/4207* (2013.01)

(58) Field of Classification Search
CPC .... A61F 2002/30299; A61F 2002/3039; A61F 2002/304
See application file for complete search history.

(56) References Cited

U.S. PATENT DOCUMENTS

| | | | |
|---|---|---|---|
| 7,520,904 | B2 | 4/2009 | Christensen |
| 7,534,246 | B2 | 5/2009 | Reiley et al. |
| 9,655,734 | B2 | 5/2017 | Smirthwaite |
| 2003/0204265 | A1 | 10/2003 | Short et al. |
| 2005/0085926 | A1 | 4/2005 | Christensen |
| 2007/0112431 | A1 | 5/2007 | Kofoed |
| 2007/0173944 | A1 | 7/2007 | Keller et al. |
| 2008/0103603 | A1 | 5/2008 | Hintermann |
| 2008/0109081 | A1 | 5/2008 | Bao et al. |
| 2010/0204799 | A1 | 8/2010 | Keller et al. |
| 2011/0035019 | A1 | 2/2011 | Goswami et al. |
| 2012/0010718 | A1 | 1/2012 | Still |
| 2015/0057761 | A1 | 2/2015 | Smirthwaite |

FOREIGN PATENT DOCUMENTS

| | | |
|---|---|---|
| EP | 1658023 A1 | 5/2006 |
| EP | 2536362 A1 | 8/2011 |
| GB | 2479899 A | 11/2011 |
| WO | WO-9918895 A1 | 4/1999 |
| WO | WO-03063741 A1 | 8/2003 |
| WO | WO-2007068440 A1 | 6/2007 |
| WO | WO-2011101699 A1 | 8/2011 |
| WO | WO-20111101699 A1 | 8/2011 |
| WO | WO-2013150308 A1 | 10/2013 |

OTHER PUBLICATIONS

"Chinese Application Serial No. 201380018651.7, Office Action dated Nov. 2, 2016", (With English Translation), 8 pgs.
"European Application Serial No. 13719138.3, Office Action dated Mar. 20, 2017", 6 pgs.
"Australian Application Serial No. 2013245411, Response filed May 19, 2017 to First Examiners Report dated Oct. 13, 2016", 19 pgs.
"European Application Serial No. 13719138.3, Response filed Jul. 20, 2017 to Office Action dated Mar. 20, 2017", 15 pgs.
"United Kingdom Application Serial No. 1206127.1, Office Action dated May 19, 2017", 3 pgs.
"U.S. Appl. No. 14/390,202 Response filed Sep. 2, 2016 to Non Final Office Action dated Jun. 3, 2016", 8 pgs.
"U.S. Appl. No. 14/390,202, Final Office Action dated Feb. 12, 2016", 13 pgs.
"U.S. Appl. No. 14/390,202, Non Final Office Action dated Jun. 3, 2016", 12 pgs.
"U.S. Appl. No. 14/390,202, Non Final Office Action dated Jul. 30, 2015", 16 pgs.
"U.S. Appl. No. 14/390,202, Notice of Allowance dated Jan. 17, 2017", 5 pgs.
"U.S. Appl. No. 14/390,202, Preliminary Amendment filed Oct. 2, 2014", 7 pgs.
"U.S. Appl. No. 14/390,202, Response filed May 12, 2016 to Final Office Action dated Jan. 12, 2016", 9 pgs.
"U.S. Appl. No. 14/390,202, Response to Non Final Office Action dated Jul. 30, 2015", 9 pgs.
"Chinese Application Serial No. 201380018651.7, Office Action dated Apr. 28, 2016", (English Translation), 3 pgs.
"Chinese Application Serial No. 201380018651.7, Office Action dated Aug. 25, 2015", (W/ English Translation), 9 pgs.
"Chinese Application Serial No. 201380018651.7, Response filed Jan. 11, 2016 to Office Action dated Aug. 25, 2015", (W/ English Translation of Claims), 13 pgs.
"European Application Serial No. 13719138.3, Office Action dated Nov. 14, 2014", 2 pgs.
"European Application Serial No. 13719138.3, Response filed Apr. 21, 2015 to Office Action dated Nov. 14, 2014", 9 pgs.
"International Application Serial No. PCT/GB2013/050885, International Preliminary Report on Patentability dated Oct. 16, 2014", 8 pgs.
"International Application Serial No. PCT/GB2013/050885, International Search Report dated Aug. 1, 2013", 4 pgs.
"International Application Serial No. PCT/GB2013/050885, Written Opinion dated Aug. 1, 2013", 6 pgs.
"United Kingdom Application Serial No. 1206127.1, Search Report dated Jul. 23, 2012" 1 pg.
"Canadian Application Serial No. 2,869,107, Office Action dated Apr. 18, 2018", 3 pgs.

PROSTHETIC ANKLE COMPONENTS

The present invention relates to a prosthetic ankle component and particularly but not exclusively to a prosthetic ankle component suitable for use in a total ankle replacement.

BACKGROUND TO THE INVENTION

It is known to replace diseased or damaged articulating surfaces of an ankle joint with prosthetic components. For example, the prosthesis may comprise a tibial component implanted into the tibia of the patient and a talar component implanted into the talus of the patient. In addition, a bearing insert may be provided between the tibial and talar components.

The insert may be fixed with respect to the tibial component. Such a fixed insert may comprise an articulating surface for engagement with a corresponding articulating surface on the talar component. Alternatively, the insert may be free to move with respect to the tibial component. Such an unconstrained insert may comprise two articulating surfaces, one for engaging each of the tibial and talar components. As a result, the unconstrained insert may provide improved articulation thanks to the additional degrees of freedom.

However, there is a risk that unconstrained mobile bearing inserts may become dislodged during use and for this reason such unconstrained inserts are presently not permitted by one or more regulation authorities, at least not without a lengthy approval process. Furthermore, a fixed insert requires accurate placement during surgery as the insert is not free to move once installed. The accurate placement required is difficult and time consuming to achieve and costly to subsequently correct.

There is also the issue of the limited access available to a surgeon when performing an ankle replacement operation. Unlike the knee, which thanks to its greater range of articulation is able to expose a greater working area for the surgeon, the ankle presents a smaller access area to the surgeon. The present invention also seeks to address this issue.

SUMMARY OF INVENTION

According to a first aspect of the present invention, there is provided a first prosthetic ankle component comprising:
a first bearing surface configured to engage, e.g. slidably engage, a second bearing surface of a second prosthetic ankle component, e.g. when in an installed configuration; and
one or more protrusions protruding from the first bearing surface, the protrusions being configured to be received by one or more corresponding receiving portions provided on the second prosthetic ankle component,
wherein the one or more protrusions are further configured such that the interaction with the receiving portions permits the first and second prosthetic ankle components to slide with respect to one another in an interface plane defined by the interface between the first and second bearing surfaces, and wherein the protrusions are further configured to restrict the first and second prosthetic ankle components moving away from one another in a direction with a component perpendicular to the interface plane.

According to a second aspect of the present invention, there is provided a second prosthetic ankle component comprising:
a second bearing surface configured to engage, e.g. slidably engage, a first bearing surface of a first prosthetic ankle component, e.g. when in an installed configuration; and
one or more receiving portions provided on the second prosthetic ankle component, the receiving portions being configured to receive one or more corresponding protrusions protruding from the first bearing surface of the first prosthetic ankle component,
wherein the one or more receiving portions are further configured such that the interaction with the one or more protrusions permits the first and second prosthetic ankle components to slide with respect to one another in an interface plane defined by the interface between the first and second bearing surfaces, and wherein the receiving portions are further configured to restrict the first and second prosthetic ankle components moving away from one another in a direction with a component perpendicular to the interface plane, According to a third aspect of the present invention, there is provided a first prosthetic ankle component comprising:
a first bearing surface configured to engage, e.g. siidably engage, a second bearing surface of a second prosthetic ankle component, e.g. when in an installed configuration; and
one or more protrusions or receiving portions, the protrusions or receiving portions being configured to engage a respective receiving portion or protrusion provided on the second prosthetic ankle component,
wherein the one or more protrusions or receiving portions are further configured such that the interaction with the respective receiving portion or protrusion permits the first and second prosthetic ankle components to slide with respect to one another in an interface plane defined by the interface between the first and second bearing surfaces, and wherein the protrusions or receiving portions are further configured to restrict the first and second prosthetic ankle components moving away from one another in a direction with a component perpendicular to the interface plane.

The one or more receiving portions may be in the form of a slot, e.g. provided in the second bearing surface of the second prosthetic ankle component. Alternatively, the receiving portions may be in form of a receiving surface, e.g. provided on a surface of the second prosthetic ankle component facing away from the first prosthetic ankle component. Such receiving surfaces may be provided at edges of the second prosthetic ankle component.

The first and/or second prosthetic ankle component may further comprise a lip. The lip may be provided at or towards an edge of the first and/or second bearing surface respectively. The lip may be configured to limit sliding movement of the first and second prosthetic ankle components. The lip may be configured such that during assembly of the first and second prosthetic ankle components an edge of the first or second bearing surface opposite the lip may ride over the lip. The lip may be further configured such that the first and second prosthetic ankle components may resiliently lock together, e.g. by virtue of the edge of the opposing bearing surface riding over the lip during assembly of the first and second prosthetic ankle components.

The protrusions and/or receiving portions cross-sectional shape, e.g. in a plane perpendicular to the respective bearing surface, may be larger at an end of the protrusion or receiving portion away from the respective bearing surface. The protrusions and receiving portions may therefore interlock. By way of example, the protrusions and/or receiving portions may have a T-shaped or L-shaped cross-section or the protrusions and/or receiving portions may have a tapered cross-section. The protrusions and/or receiving portions may be elongate, e.g. extending along at least a portion of the respective bearing surface. The receiving portions may be longer than the protrusions to permit the movement of the protrusions relative to the receiving portions. The protrusions cross-sectional shape, e.g. in a plane substantially parallel to the respective bearing surface, may be circular. For example, the protrusion may be mushroom shaped.

The one or more protrusions may comprise a neck portion and a head portion. The neck portion may have a length, e.g. in a substantially anterior-posterior direction, that is greater than, equal to, or less than the length of the head portion.

In the case of the receiving portions being a slot, an opening to the slot may be provided in an end wall of the second prosthetic ankle component. The opening may be arranged to receive the protrusion during assembly of the first and second prosthetic ankle components.

The protrusions and/or receiving portions may be configured to permit relative rotation between the first and second prosthetic ankle components. For example, the protrusion may be circular in a plane parallel to the bearing surface and/or the protrusion may not form a tight fit in the slot. The protrusions and/or receiving portions may be configured such that the amount of relative rotation between the first and second prosthetic ankle components may be limited. For example, the protrusion may not form a tight fit in the slot and corners of the protrusion may abut sidewalls of the slot to limit the relative rotation. Alternatively, the protrusion may form a tight fit in the slot, e.g. so that relative rotation between the first and second prosthetic ankle components may not be permitted.

One of the first or second prosthetic ankle component may comprise a further bearing surface configured to engage a third prosthetic ankle component. The one of the first or second prosthetic ankle component may be a bearing insert which may be provided between the other of the first and second prosthetic ankle components and the third prosthetic ankle component, The bearing insert may be a mobile bearing insert, e.g. that may move with respect to the first and/or second prosthetic ankle components.

The other of the first or second prosthetic ankle component may be configured to be connected to the tibia or talus of a patient. The third prosthetic ankle component may be configured to be connected to the other of the tibia or talus of the patient. The first, second and/or third prosthetic ankle components may be components of a total ankle replacement.

The further bearing surface may be provided on a surface of the first or second prosthetic ankle component opposite the respective first or second bearing surface. The further bearing surface may extend over the respective protrusion or receiving portion on the opposite bearing surface.

The first, second and/or further bearing surfaces may be a surface which contacts a corresponding bearing surface, e.g. for the purpose of enabling an articulation.

A prosthetic ankle assembly may comprise the above-mentioned first prosthetic ankle component and the above-mentioned second prosthetic ankle component. The prosthetic ankle assembly may further comprise the above-mentioned third prosthetic ankle component..

According to a fourth aspect of the present invention there is provided a method of installing the first, second and/or third prosthetic ankle components mentioned above.

BRIEF DESCRIPTION OF THE DRAWINGS

For a better understanding of the present invention, and to show more clearly how it may be carried into effect, reference will now be made, by way of example, to the following drawings in which:—

DETAILED DESCRIPTION OF EMBODIMENTS

With reference to FIGS. 1 to 4, a prosthetic ankle assembly comprises a first prosthetic ankle component 10 and a second prosthetic ankle component 20, which may be implanted into the ankle joint of a patient. The prosthetic ankle assembly may further comprise a third prosthetic ankle component 30 (depicted in FIGS. 3 to 6). The first prosthetic ankle component 10 may be implanted into the tibia of the patient and may thus form a tibial component. The third prosthetic ankle component 30 may be implanted into the talus of the patient and may thus form a talar component. The second prosthetic ankle component 20 may be provided between the first and further ankle components 10, 30.

The first prosthetic ankle component 10 comprises a first bearing or articulating surface 12 and the second prosthetic ankle component 20 comprises a second bearing or articulating surface 22. The first bearing surface 12 is configured to engage the second bearing surface 22 such that the first prosthetic ankle component 10 may articulate with respect to the second prosthetic ankle component 20, for example when the prosthetic ankle assembly is implanted within the patient and during use of the ankle joint. In a similar fashion the second prosthetic ankle component 20 comprises a further bearing or articulating surface 24, which is configured to engage a corresponding third bearing or articulating surface 32 provided on the third prosthetic ankle component 30.

The first prosthetic ankle component 10 comprises a protrusion 16 which protrudes from the first bearing surface 12. The protrusion 16 may or may not be integral with the first prosthetic ankle component 10, e.g. the protrusion may be selectively applied to the first prosthetic ankle component, which may otherwise be used without a protrusion depending on the requirements of the patient.

The second prosthetic ankle component 20 comprises a receiving portion, which may be in the form of a receiving surface, groove, slit, channel, recess, slot or any other receiving portion capable of receiving the protrusion 16. In the example depicted, the receiving portion is in the form of a slot 26, which may be formed on the second bearing surface 22, e.g. in a substantially anterior-posterior direction. The protrusion 16 and/or slot 26 may be provided on the centreline of the prosthetic ankle assembly. In an alternative arrangement (not shown), two or more protrusions may be provided at opposite edges of the first bearing surface and said protrusions may engage corresponding receiving surfaces provided on the second prosthetic ankle component. In either case, the protrusion 16 on the first bearing surface 12 is configured to engage the receiving portion, e.g. slot 26, such that the protrusion may slide with respect to the receiving portion, e.g. in the slot. Likewise, the receiving portion, e.g. slot 26, is configured to receive the protrusion 16 protruding from the first bearing surface 12.

The further bearing surface 24 may be provided on a surface of the second prosthetic ankle component 20 opposite the second bearing surface 22. As such, the further bearing surface 24 may extend over the slot 26 on the second bearing surface 22.

Figure 3:
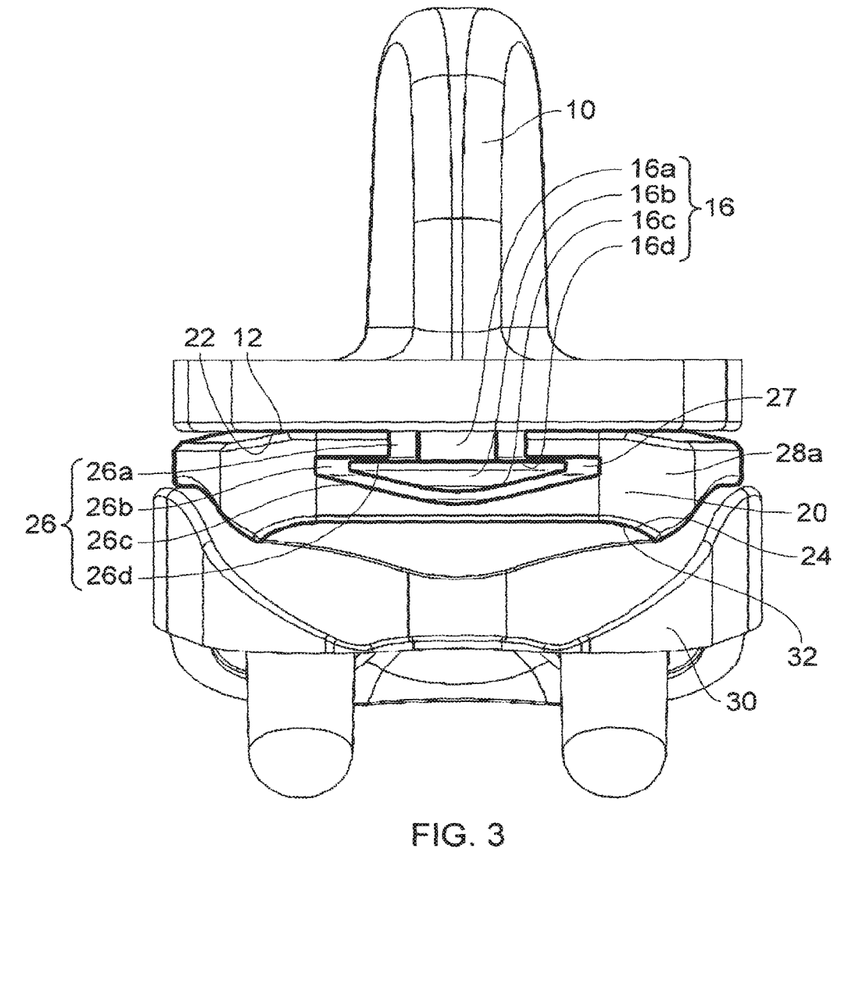
FIG. 3 is an end on (posterior) view of a prosthetic ankle assembly according to an example of the present invention.

As depicted in FIG. 3, the cross-sectional shape of the protrusion 16, in a plane perpendicular to the first bearing surface 12 (and perpendicular to the length of the slot), is larger at an end of the protrusion away from the first bearing surface. Similarly, the cross-sectional shape of the slot 26, in a plane perpendicular to the second bearing surface 22, is larger at an end of the slot away from the second bearing surface 22. As a result, the protrusion 16 and slot 26 may therefore interlock.

By way of example, the protrusion 16 and slot 26 may have a tapered cross-section, e.g. with one or more sloping sidewalls. Alternatively, the protrusion 16 and slot 26 may have a T-shaped or L-shaped cross-section. In other words, the protrusion 16 may comprise a neck portion 16a and a head portion 16b. The head portion 16b may be wider than the neck portion 16a, e.g. in a substantially medial-lateral direction. The neck portion 16a may be provided between the first bearing surface 12 and the head portion 16b. Accordingly, the head portion 16b may be provided on the top of the protrusion 16.

In a similar fashion, the slot 26 may comprise a narrow portion 26a and a wide portion 26b. The wide portion 26b may be wider than the narrow portion 26a, e.g. in a substantially medial-lateral direction. The narrow portion 26a may be provided between the second bearing surface 22 and the wide portion 26b. Accordingly, the wide portion 26b may be provided at the bottom of the slot 26 and the wide portion may form a floor 26c of the slot. As shown, the floor 26c of the slot may comprise a curved, e.g. concave, profile. Similarly, the head portion 16b may comprise a curved, e.g. convex, top surface 16c.

The protrusion 16 comprises a first abutment surface 16d which is formed by a surface of the head portion 16b that faces the first bearing surface 12. Likewise, the slot 26 comprises a second abutment surface 26d which is formed by a surface at the interface between the narrow and wide portions 26a, 26b and which faces the floor 26c of the slot 26. The first and second abutment surfaces 16d, 26d may engage each other so as to limit or prevent the first and second prosthetic ankle components 10, 20 moving away from one another, e.g. in a direction substantially perpendicular to the first and second bearing surfaces 12, 22. The present invention may therefore benefit from the advantages of having a mobile bearing insert, but with the added advantage of the first and second prosthetic ankle components 10, 20 being constrained together by the interaction between the protrusion and slot 16, 26. (NB, a mobile bearing insert is a bearing insert that may move relative to other components when implanted into the patient and during use of the prosthesis.)

The protrusion 16 and/or slot 26 may be elongate, e.g. extending along at least a portion of the respective bearing surface 12, 22. For example, the neck portion 16a and/or head portion 16b of the protrusion may be elongate, e.g. in a substantially anterior-posterior direction. In the particular example shown, the neck portion 16a and head portion 16b may have the same length in the substantially anterior-posterior direction, although it is also envisaged that the neck portion may have a length that is greater or less than the length of the head portion. However, the protrusion 16 may not be elongate, e.g. with the neck portion 16a and/or head portion 16b having a circular or square cross-sectional shape, i.e. in a plane substantially parallel to the first bearing surface. For example, the protrusion 16 may be mushroom shaped. In any event, the slot 26 is longer than the protrusion 16 to permit sliding movement of the protrusion in the slot. In this way, the protrusion 16 and slot 26 are configured such that their mutual interaction permits the first and second prosthetic ankle components 10, 20 to slide with respect to one another in an interface plane defined by the interface between the first and second bearing surfaces 12, 22. Accordingly, the first and second prosthetic ankle components 10, 20 may slide with respect to one another in the direction of the slot 26.

In addition to the above described sliding action, the protrusion 16 and/or slot 26 may be configured to permit relative rotation between the first and second prosthetic ankle components 10, 20. For example, as mentioned above, the protrusion 16 may be circular in a plane parallel to the first bearing surface 12, thereby permitting relative rotation between the first and second prosthetic ankle components 10, 20. Alternatively (or additionally), the protrusion 16 may not form a tight fit in the slot 26, e.g. with the neck and head portions 16a, 16b of the protrusion 16 being smaller in width than the narrow and wide portions 26a, 26b of the slot 26 respectively.

However, whilst a degree of rotation between the first and second prosthetic ankle components 10, 20 may be desirable to increase the articulation of the prosthetic ankle, the protrusion 16 and/or slot 26 may be configured such that the amount of relative rotation between the first and second prosthetic ankle components may be limited. For example, the protrusion 16 may not form a tight fit in the slot 26. In particular, whilst the neck and head portions 16a, 16b of the protrusion 16 may be smaller in width than the narrow and wide portions 26a, 26b of the slot 26 respectively, the neck and/or head portions 16a, 16b of the protrusion 16 may be sized with respect to the narrow and wide portions 26a, 26b of the slot 26 respectively such that relative rotation is limited. In this regard, corners of the neck and/or head portions 16a, 16b of the protrusion 16 may abut sidewalls of the narrow and wide portions 26a, 26b of the slot 26 respectively to limit the relative rotation between the first and second prosthetic ankle components 10, 20. However, the corners of the neck and/or head 16b may be curved to prevent the protrusion 16 jamming in the slot 26.

In an alternative arrangement (not shown) the protrusion may form a tight fit in the slot, e.g. so that relative rotation between the first and second prosthetic ankle components may not be permitted.

Figure 2:
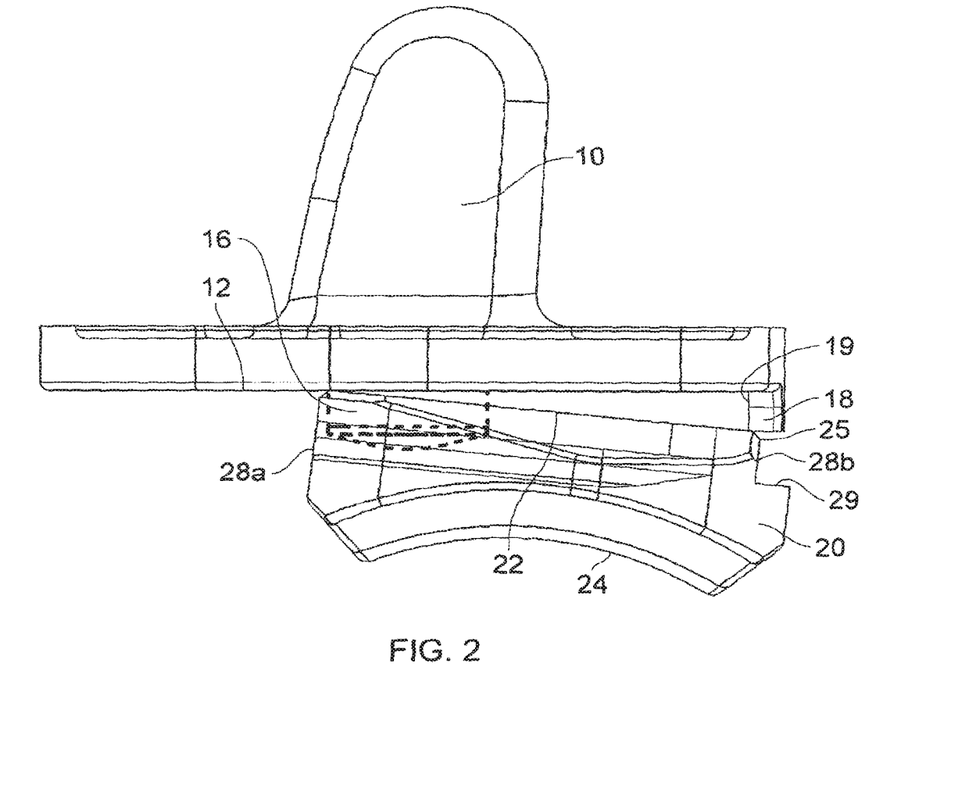
FIG. 2 is a side (medial or lateral) view of the first and second prosthetic ankle components during assembly according to an example of the present invention.

To permit assembly, an opening 27 to the slot 26 may be provided in a first end wall 28a of the second prosthetic ankle component 20. The first end wall 28a and hence opening 27 may be angled or substantially perpendicular to the second bearing surface 22 and slot 26. Accordingly, the opening 27 may be arranged to receive the protrusion 16 during assembly of the first and second prosthetic ankle components 10, 20, e.g. as depicted in FIG. 2. The opening 27 may be provided at a posterior end of the second prosthetic ankle component 20. By contrast, the slot 26 may be closed at the apposite end of the slot to the opening 27, e.g. at the anterior end of the slot, thereby limiting bearing motion posteriorly.

During an ankle replacement operation, the surgeon may only have limited access to the ankle joint from the anterior side. By providing the opening 27 in the first end wall 28a, the surgeon may readily slide the second prosthetic ankle component 20 onto the first prosthetic ankle component 10.

Figure 1:
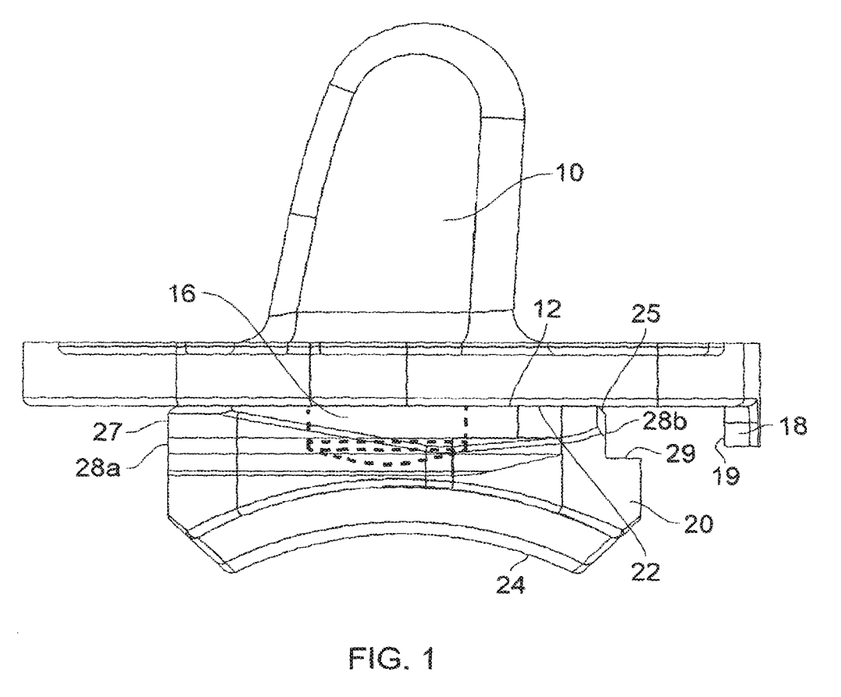
FIG. 1 is a side (medial or lateral) view of first and second prosthetic ankle components after assembly according to an example of the present invention.
Figure 4:
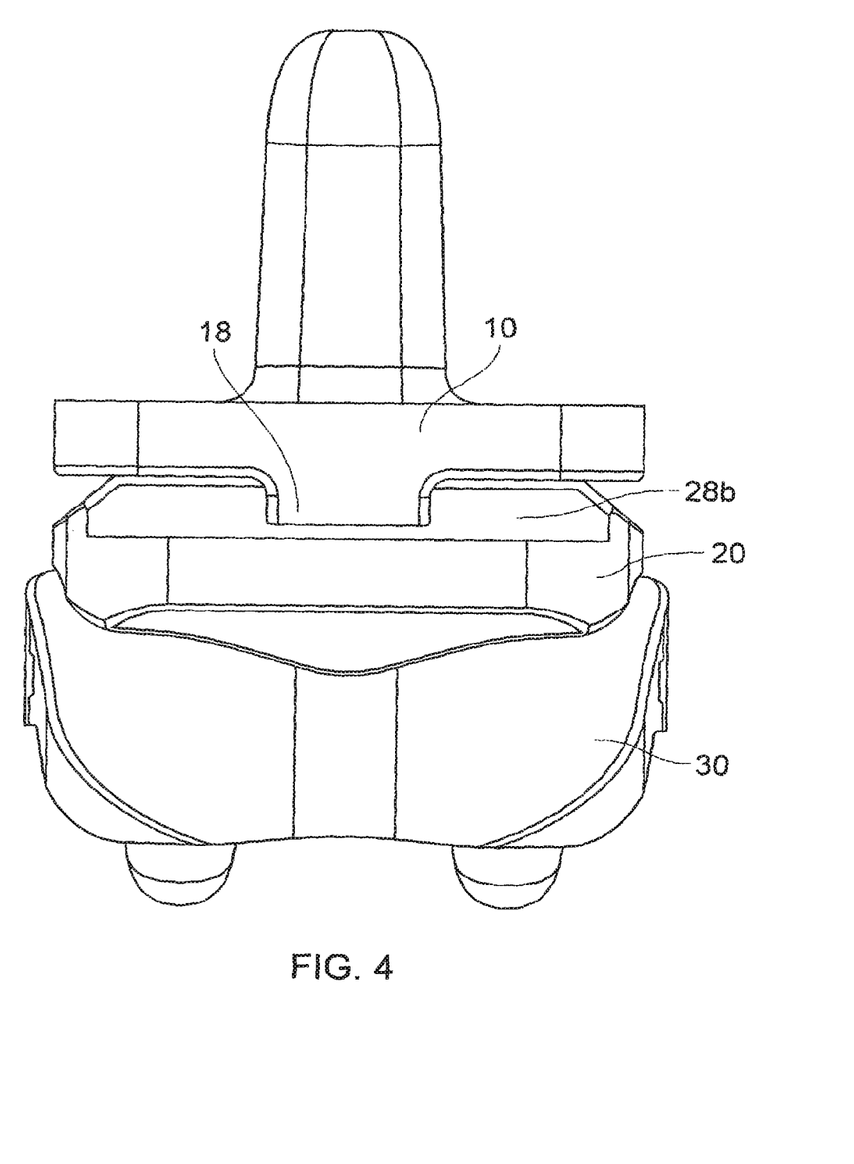
FIG. 4 is an end on (anterior) view of the prosthetic ankle assembly according to an example of the present invention.
Figure 5:
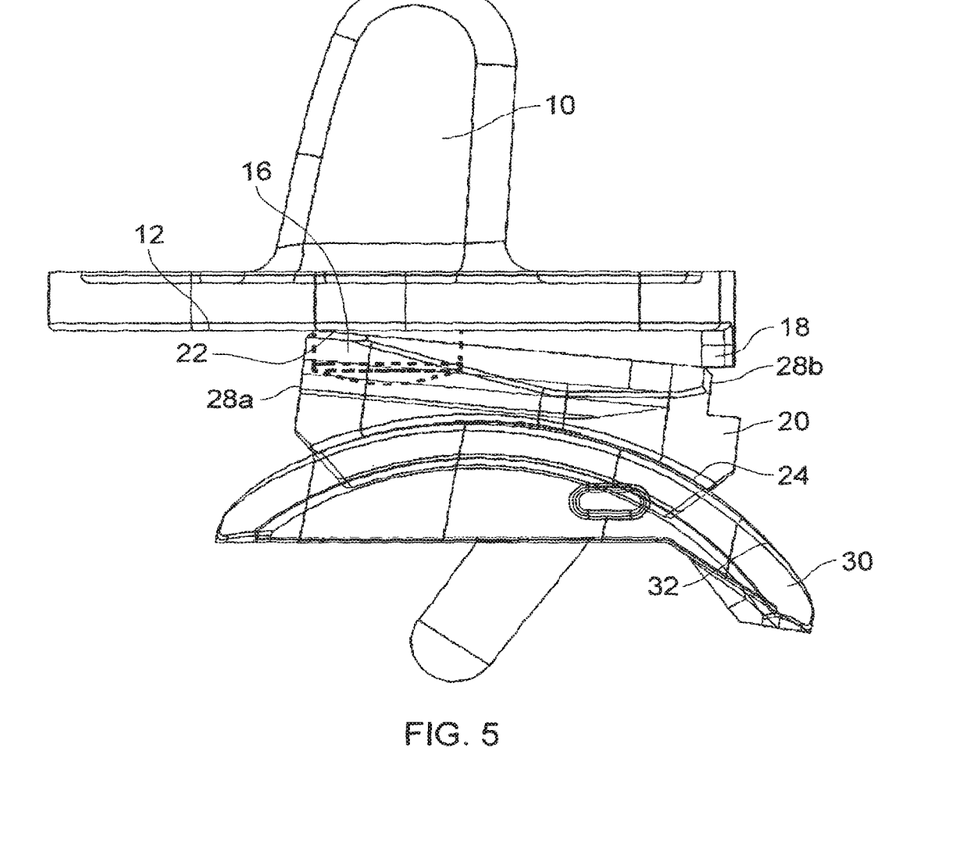
FIG. 5 is a side (medial or lateral) view of the prosthetic ankle assembly during assembly according to an example of the present invention.
Figure 6:
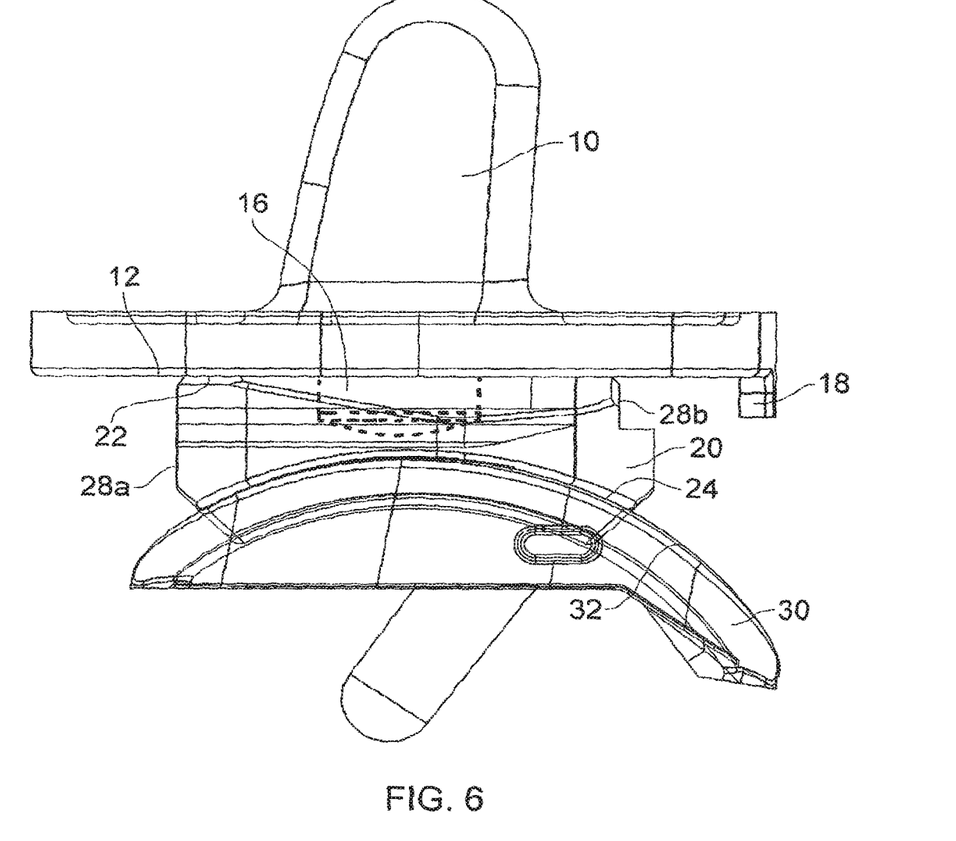
FIG. 6 is a side (medial or lateral) view of the prosthetic ankle assembly after assembly according to an example of the present invention.

As shown in FIGS. 1, 2 and 4, the first prosthetic ankle component 10 may further comprise a lip 18. The lip 18 may be provided at or towards an edge of the first bearing surface 12 and the lip 18 may be provided at an anterior end of the prosthetic ankle. The lip 18 may protrude from an edge of the first bearing surface 12 and may provide an abutment surface 19 against which an edge of the second prosthetic ankle component 20 may abut. Accordingly, the lip 18 may be configured to limit sliding movement of the first and second prosthetic ankle components 10, 20. The second prosthetic ankle component 20 may comprise an indent 29 which may correspond to and receive the lip 18 and abutment surface 19.

As depicted in FIG. 2, the lip 18 may be configured such that during assembly of the first and second prosthetic ankle components 10, 20, an edge 25 of the second bearing surface 22 may ride over the lip 18. The edge 25 may be the edge between the second bearing surface 22 and a second end wall 28b of the second prosthetic ankle component 20. The second end wall 28b is opposite the first end wall 28a which comprises the opening 27 of the second prosthetic ankle component 20. The lip 18 may be further configured such that the first and second prosthetic ankle components 10, 20 may resiliently lock together, e.g. by virtue of the edge 25 of the second prosthetic ankle component 20 riding over the lip 18 during assembly of the first and second prosthetic ankle components. For example, at least a portion of the second prosthetic ankle component 20 may flex during assembly to allow the edge 25 to ride over the lip 18. At least a portion of the second prosthetic ankle component 20 may be made from a resilient material, such as a polymer. In a particular example the second prosthetic ankle component 20 may be made from an Ultra-high-molecular-weight polyethylene (UHMWPE) such as a highly cross-linked UHMWPE. In a further example, the second prosthetic ankle component 20 may be made from Polyetheretherketone (PEEK).

It will be appreciated that the protrusion 16, slot 26 and lip 18 may prevent the second prosthetic ankle component 20 from becoming dislodged during use. However, the second prosthetic ankle component 20 may subsequently be dislodged from the first prosthetic ankle component 10, e.g. by a surgeon using a tool to prize the first and second prosthetic ankle components apart.

Although in the example shown the first and second prosthetic ankle components 10, 20 comprise the protrusion and slot 16, 26 respectively, an alternative example (not shown) may be arranged in the opposite manner with the first and second prosthetic ankle components comprising the slot and protrusion respectively. Equally, the lip 18 may be provided on either of the first or second prosthetic ankle components 10, 20. In a further alternative arrangement, the first prosthetic ankle component 10 may be implanted into the talus and the third prosthetic ankle component 30 may be implanted into the tibia.

Figure 7A:
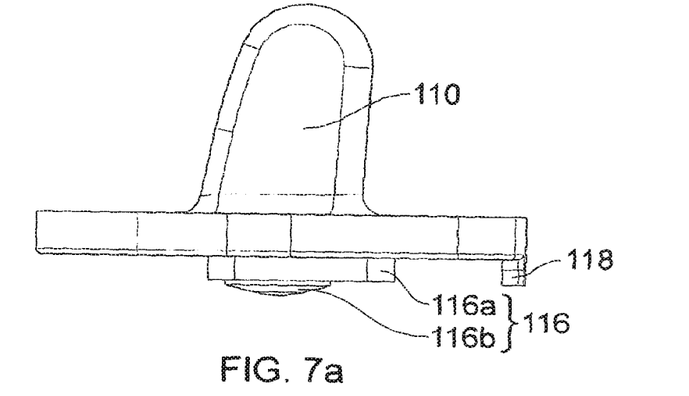
FIGS. 7a, 7b and 7c are side (medial or lateral), end on (posterior) and plan views respectively of a first prosthetic ankle component according to a further example of the present invention (NB, the lip has been removed from FIG. 7b for the sake of clarity)
Figure 7B:
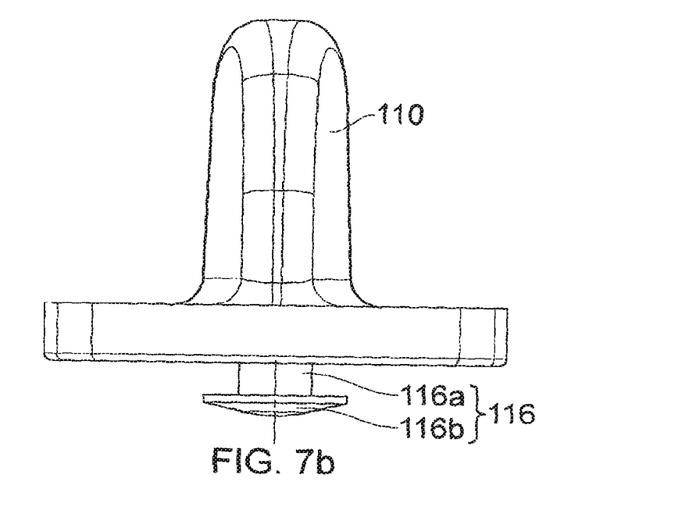
Figure 7C:
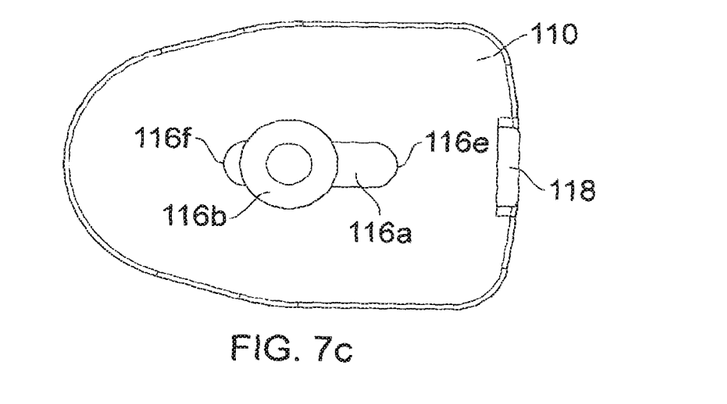
Figure 8A:
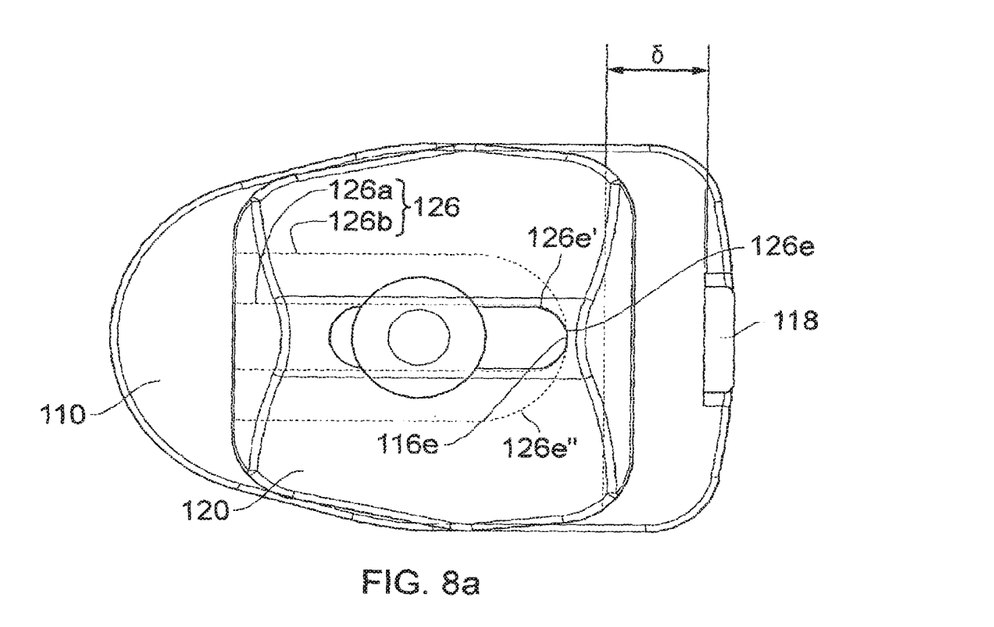
FIGS. 8a and 8b are plan views of the first and second prosthetic ankle components according to the further example of the present invention with FIGS. 8a and 8b depicting translation and rotation of the second component with respect to the first component respectively.
Figure 8B:
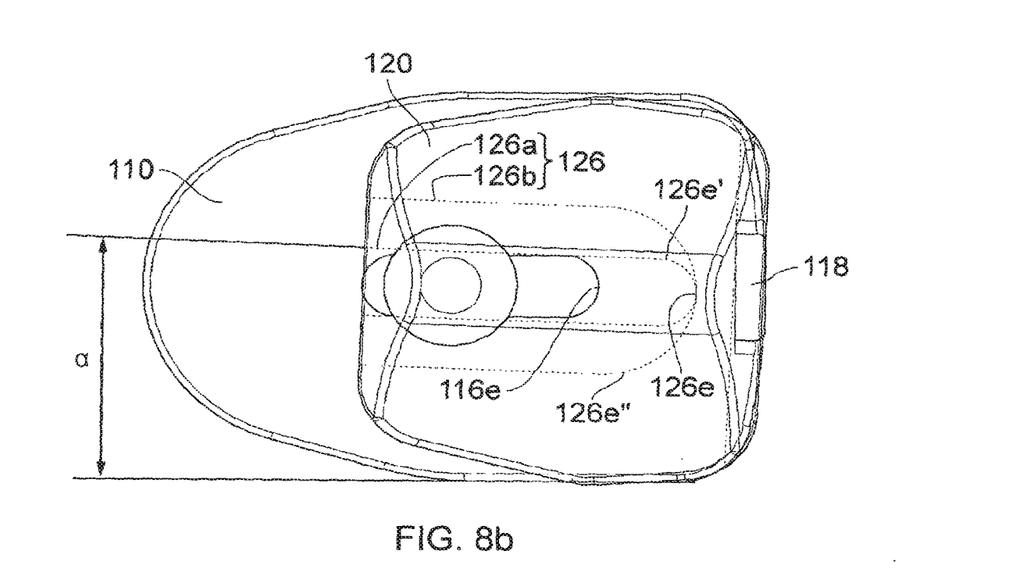

In a further example depicted in FIGS. 7 and 8, the neck portion 116a of the first prosthetic ankle component protrusion 116 may have a length in a substantially anterior-posterior direction that is greater than the length of the head portion 116b of the protrusion. The neck portion 116a may be elongate, for example, as depicted the neck portion may be obround shaped (i.e. an oblong with rounded ends). By contrast, the head portion 116b may not be elongate, for example the head portion may be circular, e.g. in a plane parallel to the bearing surface. The further example of FIGS. 7 and 8 is otherwise substantially the same as the prosthetic ankle assembly described above and features of the above example may apply equally to the further example. In particular, the first ankle component 110 of the further example may slidably engage a second prosthetic ankle component 120 similar to that described above.

As best viewed in FIG. 7c, the neck portion 116a may comprise curved ends 116e, 116f. Likewise, with reference to FIGS. 8a and 8b, the corresponding slot 126 in the second prosthetic ankle component 120 may also comprise a curved end 126e. The narrow portion 126a of the slot 126 may have a curved end 126e' with a first radius of curvature, whilst the wide portion 126b may have a curved end 126e" with a second radius of curvature, which may be greater than the first radius of curvature. As depicted, apexes of the curved ends 126e' and 126e" may coincide, or alternatively, the apexes of the curved ends 126e' and 126e" may be spaced apart.

Referring to FIGS. 8a and 8b, translation and/or rotation of the second prosthetic ankle component 120 may be permitted with respect to the first prosthetic ankle component 110. For example, as depicted in FIG. 8a, the protrusion and slot arrangement of the further example may permit translation of the second prosthetic ankle component 120 with respect to the first ankle component 110 by an amount δ. The neck portion 116a may limit the travel of the second prosthetic ankle component 120, e.g. in the anterior-posterior direction. The neck portion end 116e may abut the closed end 126e of the slot 126, in particular, the end 126e' of the slot narrow portion 126a. By contrast, the second prosthetic ankle component 120 may abut the lip 118 of the first ankle component 110 to limit the travel in the opposite direction.

As depicted in FIG. 8b, the protrusion and slot arrangement may permit rotation of the second prosthetic ankle component 120 with respect to the first ankle component 110. The neck portion 116a may be narrower than the corresponding narrow portion 126a of the slot 126 (e.g. in a substantially medial-lateral direction), thereby permitting rotation of the second prosthetic ankle component 120 with respect to the first prosthetic ankle component 110. The protrusion neck portion 116a and/or slot narrow portion 126a width and/or the protrusion neck portion length may be sized so as to limit the degree of rotation by a predetermined amount. The neck portion may limit rotation of the second prosthetic ankle component 120 from an aligned position with respect to the first prosthetic ankle component 110 by an angle of α degrees, for example, the neck portion may limit the rotation by 2 degrees. In other words, the second ankle component may rotate by a total of 2α degrees, e.g. 4 degrees, from one extreme to another.

As depicted, side walls of the neck portion 116a and narrow portion 126a may be substantially parallel, however, in an alternative arrangement the sidewalls of the neck portion and/or narrow portion may be tapered. In this way the amount of permitted rotation between the first and second prosthetic ankle components may be varied at particular translational positions.

It will be appreciated that the translation and/or rotation of the further example depicted in FIGS. 7 and 8 may better match the anatomical range of motion.

The invention claimed is:

1. A first prosthetic ankle component comprising:
a first bearing surface configured to slidably engage a second bearing surface of a second prosthetic ankle component when in an installed configuration; and
one or more protrusions protruding from the first bearing surface, the protrusions being configured to be received by one or more corresponding receiving portions provided on the second prosthetic ankle component,
wherein the one or more protrusions are further configured such that the interaction with the receiving portions permits the first and second prosthetic ankle components to slide with respect to one another in an interface plane defined by the interface between the first and second bearing surfaces, and wherein the protrusions are further configured to restrict the first and second prosthetic ankle components moving away from one another in a direction with a component perpendicular to the interface plane, and wherein the protrusion includes an abutment surface configured to abut a closed end of the of the second prosthetic ankle component to limit a sliding movement in a first direction; and
wherein the first prosthetic ankle component further comprises a lip, the lip being provided at or towards an edge of the first bearing surface, the lip being configured to limit sliding movement of the first and second prosthetic ankle components in a second direction which is opposite the first direction by having an abutment surface configured to abut a surface of the second prosthetic component, wherein the abutment surface of the protrusion and the abutment surface of the lip are opposed to and facing each other so as to limit sliding movement in both the first direction and the second direction which is opposite the first direction.

2. The first prosthetic ankle component of claim 1, wherein the lip is configured such that during assembly of the first and second prosthetic ankle components an edge of the second bearing surface opposite the lip may ride over the lip.

3. The first prosthetic ankle component of claim 2, wherein the lip is further configured such that the first and second prosthetic ankle components resiliently lock together by virtue of the edge of the second bearing surface riding over the lip during assembly of the first and second prosthetic ankle components.

4. The first prosthetic ankle component of claim 1, wherein the one or more protrusions and/or receiving portions cross-sectional shape is larger at an end of the protrusion or receiving portion away from the respective bearing surface.

5. The first prosthetic ankle component of claim 4, wherein the one or more protrusions and/or receiving portions have a T-shaped or L-shaped cross-section.

6. The first prosthetic ankle component of claim 4, wherein the one or more protrusions comprise a neck portion and a head portion, the neck portion having a length that is greater than the length of the head portion.

7. The first prosthetic ankle component of claim 1, wherein the one or more receiving portions are in the form of a slot provided in the first bearing surface of the first prosthetic ankle component.

8. The first prosthetic ankle component of claim 7, wherein an opening to the slot is provided in an end wall of the first prosthetic ankle component, the opening being arranged to receive a corresponding protrusion during assembly of the first and second prosthetic ankle components.

9. The first prosthetic ankle component of claim 1, wherein the protrusions and/or receiving portions are configured to permit relative rotation between the first and second prosthetic ankle components.

10. The first prosthetic ankle component of claim 9, wherein the protrusions and/or receiving portions are configured such that an amount of relative rotation between the first and second prosthetic ankle components is limited.

11. The first prosthetic ankle component of claim 1, wherein one of the first or second prosthetic ankle component comprises a further bearing surface configured to engage a third prosthetic ankle component.

12. The first prosthetic ankle component of claim 11, wherein the one of the first or second prosthetic ankle component is a bearing insert provided between the other of the first and second prosthetic ankle components and the third prosthetic ankle component.

13. The first prosthetic ankle component of claim 11, wherein the further bearing surface is provided on a surface of the first or second prosthetic ankle component opposite the respective first or second bearing surface, the further bearing surface extending over the respective protrusions or receiving portions on the second surface.

14. The first prosthetic ankle component of claim 11, wherein the other of the first or second prosthetic ankle component is configured to be connected to the tibia or talus of a patient and the third prosthetic ankle component is configured to be connected to the other of the talus or tibia of the patient.

* * * * *

UNITED STATES PATENT AND TRADEMARK OFFICE
CERTIFICATE OF CORRECTION

| | | |
|---|---|---|
| PATENT NO. | : 10,188,523 B2 | Page 1 of 1 |
| APPLICATION NO. | : 15/485647 | |
| DATED | : January 29, 2019 | |
| INVENTOR(S) | : Paul Smirthwaite | |

It is certified that error appears in the above-identified patent and that said Letters Patent is hereby corrected as shown below:

In the Claims

In Column 9, Line 38, in Claim 1, delete "of the of the" and insert --of the-- therefor Signed and Sealed this
Fourteenth Day of April, 2020

Andrei Iancu
*Director of the United States Patent and Trademark Office*